(12) United States Patent
O'Brien et al.

(10) Patent No.: US 7,727,598 B2
(45) Date of Patent: Jun. 1, 2010

(54) PARTIALLY ROLL COATED WORKPIECE AND METHODS AND SYSTEMS FOR MAKING THE SAME

(75) Inventors: Anthony O'Brien, Oranmore (IE);
Aiden Flanagan, Kilcolgan (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1065 days.

(21) Appl. No.: 11/415,110

(22) Filed: May 2, 2006

(65) Prior Publication Data

US 2007/0259125 A1 Nov. 8, 2007

(51) Int. Cl.
*B05D 1/28* (2006.01)
*B05D 7/00* (2006.01)
*B05C 1/08* (2006.01)

(52) U.S. Cl. .................. 427/428.01; 427/2.1; 427/2.24; 427/428.08; 427/428.09; 427/428.2; 118/216; 118/249; 118/256; 118/258

(58) Field of Classification Search ......... 427/2.1–2.31, 427/428.01–428.21; 118/200, 209, 224, 118/230, 232, 233, 244; 401/9–11, 208, 401/218
See application file for complete search history.

(56) References Cited

U.S. PATENT DOCUMENTS

| | | | |
|---|---|---|---|
| 5,344,062 A | | 9/1994 | Krengel et al. |
| 5,476,546 A | * | 12/1995 | Zibulla ....................... 118/668 |
| 5,830,548 A | | 11/1998 | Andersen et al. |
| 6,971,813 B2 | * | 12/2005 | Shekalim et al. ............ 401/208 |
| 6,984,411 B2 | | 1/2006 | Palasis et al. |
| 2004/0181236 A1 | * | 9/2004 | Eidenschink et al. ........ 606/108 |

FOREIGN PATENT DOCUMENTS

| | | |
|---|---|---|
| DE | 8506389 | 6/1985 |
| DE | 3813939 | 11/1989 |
| DE | 4105364 | 5/1992 |
| FR | 1427399 | 12/2007 |
| JP | 11138077 | 5/1999 |
| WO | 9103331 | 3/1991 |
| WO | 03020451 | 3/2003 |

OTHER PUBLICATIONS

International Search Report and Written Opinion in PCT/US2007/010562, dated Jan. 9, 2008.
Partial International Search Report in PCT/US2007/010562, dated Nov. 27, 2007.

* cited by examiner

*Primary Examiner*—Timothy H Meeks
*Assistant Examiner*—Cachet I Sellman
(74) *Attorney, Agent, or Firm*—Vidas, Arrett & Steinkraus

(57) ABSTRACT

The present invention is directed to methods, processes, and systems for roll coating portions of a workpiece as well as to workpieces that have themselves been roll coated in accord with the invention. Under these methods and processes of the invention, one of a roller and/or the workpiece may be moved longitudinally to apply coating to a target surface of a workpiece. In some embodiments, a plurality of rollers may be used and supported by arms. Still further, in accord with the embodiments of the present invention, a dispensing member may be provided to fluidly connect the roller with a reservoir. In still other embodiments, the workpiece may be an implantable medical device and the coating may include a therapeutic.

19 Claims, 5 Drawing Sheets

US 7,727,598 B2

PARTIALLY ROLL COATED WORKPIECE AND METHODS AND SYSTEMS FOR MAKING THE SAME

TECHNICAL FIELD

The present invention generally relates to partially coated workpieces and methods and systems for partially coating a workpiece with a coating or other treatment. More specifically, the present invention relates to workpieces, such as implantable medical devices, and methods and systems for coating these medical devices, wherein a treatment or other coating is applied to some but not all surfaces of the workpiece during a roll coating process.

BACKGROUND

Coating workpieces is an often repeated procedure in contemporary manufacturing. Workpieces may be coated by methods that include tumble coating, spray coating, dip coating, and electrostatic spraying. During each of these procedures coating is applied to the workpiece prior to the workpiece being used for an intended purpose.

When the workpiece is formed partially or completely out of lattice struts or some other open framework, each of the faces of these struts or framework is exposed to the coating. By exposing each face of the workpiece to the coating being applied, each exposed face will be covered during the coating process.

When the workpiece being coated is an implantable medical device, such as a stent, all faces of the struts that comprise the stent are coated when using the coating systems identified above. For example, when dip coating is used, each face of the stent struts will be exposed to the coating. This coating remains when the stent is removed from the dip and dries on each face of the struts. Coating may also remain in the spaces between the struts. This phenomenon is sometimes called "webbing." Here, not only are the individual struts covered, but some or all of the spaces between the struts are spanned by the coating as well.

BRIEF DESCRIPTION

The present invention is directed to methods, processes, and systems for roll coating portions of a workpiece as well as to workpieces that have themselves been roll coated in accord with the invention. Under these methods and processes, a roller and/or a workpiece may be moved longitudinally to apply coating to a target surface of the workpiece. A plurality of rollers and a dispensing member may be used when practicing the invention.

Other objects and features of the invention are also possible. The following detailed description, which, when taken in conjunction with the annexed drawings, discloses some examples of the invention.

BRIEF DESCRIPTION OF THE DRAWINGS

Referring to the drawings, which form a part of this disclosure.

DETAILED DESCRIPTION

The present invention regards roll coating one or more surfaces of a workpiece while not coating other surfaces of the workpiece. In some embodiments this may include coating the outside or side surfaces of the struts of a stent. By coating in this fashion, the amount of coating resident on the stent may be reduced. If the coating contains a therapeutic, a reduction in coating on the stent may allow the therapeutic to be delivered in a more targeted fashion after the stent is implanted in a patient because it is only resident on some but not all faces of the struts of the stent.

This selective coating of a workpiece may be accomplished in accord with the present invention by moving a roller and/or a workpiece longitudinally to apply coating to a target surface of the workpiece. A plurality of rollers may also be used and one or more of these rollers may be supported by arms. A variety of dispensing members may also be provided to fluidly connect the roller with a reservoir storing or otherwise including a coating. In some instances, the workpiece may be flexible and may deform during handling or processing. Furthermore, when the workpiece forms a lattice, irregularities and bare spots may arise-methods, processes and systems of the present invention may be used to reduce or eliminate these irregularities.

Figure 1A:
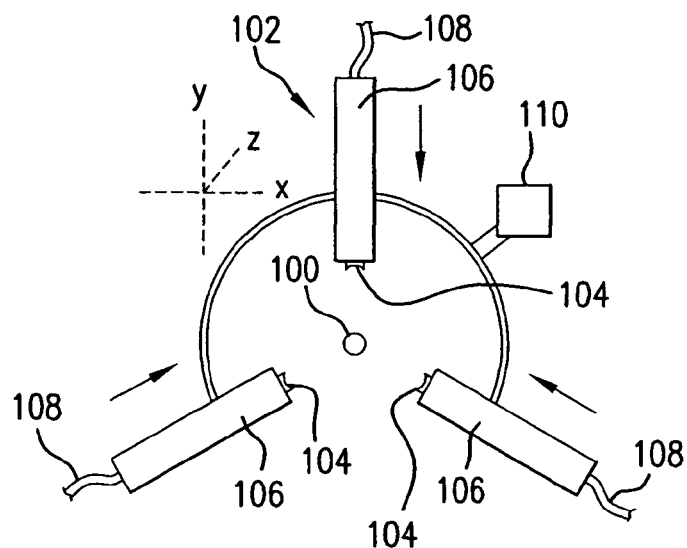
FIG. 1a is a side-view of a plurality of rollers in the open position as may be employed in accord with the invention.
Figure 1B:
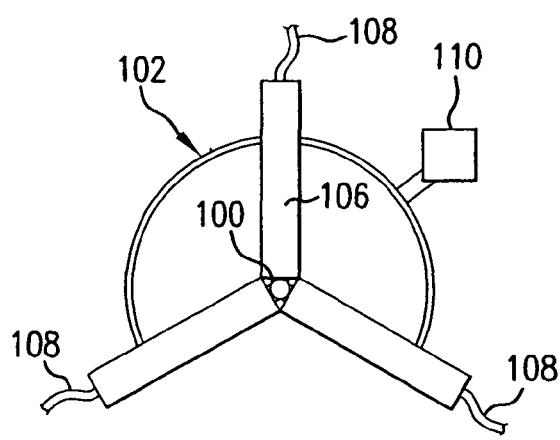
FIG. 1b is a side-view of the plurality of rollers of FIG. 1a in the closed position to engage the workpiece as may be employed in accord with the invention.

FIGS. 1a and 1b generally show a workpiece 100 surrounded by a coating assembly 102. FIG. 1a shows the assembly 102 in an open position while FIG. 1b shows the assembly 102 in a closed position. When in the closed position the workpiece 100 may be held in place by the coating assembly 102 as it is coated by the coating assembly 102. The arms 106 shown in FIGS. 1a and 1b may be arranged to move inwardly and outwardly between the open and closed positions. The direction of movement is indicated by the arrows in FIG. 1a. In the closed position, the arms 106 may contact the workpiece while in the open position the arms may allow the workpiece to be inserted and removed from the assembly 102. One or more of the arms 106 may be moved longitudinally along the workpiece 100 by the moving member 110. As one or more of the arms 106 move a thin film of coating may be distributed to the outside of the workpiece 100. This thin film of coating may be supplied to the rollers 104 during the coating process from a reservoir through the fluid passages 108. The rollers 104 may be shaped with a concave surface to allow a tubular workpiece to fit securely in the space defined by the rollers when they are in the closed position. The rollers may have other shapes as well.

The coating assembly and moving member may have various configurations and shapes in addition to what is shown in FIG. 1a and FIG. 1b. For example, the moving member may be cylindrical and may support the arms 106 from distal ends of the arms. Furthermore, the moving member may also have a sleeve or other holder upon which the stent or other workpiece may be placed for handling.

Figure 2A:
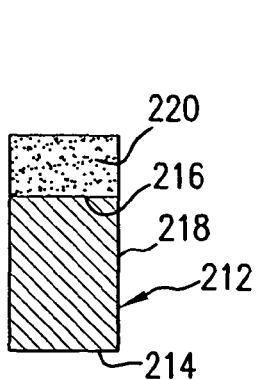
FIG. 2a is a cross-sectional view of a portion of a coated strut from a medical device that has been coated in accord with the present invention.

FIG. 2a is a side sectional view of a strut 212 of a stent that has been coated in accord with the present invention. The strut 212 in FIG. 2a has an inner surface 214, an outer surface 216, and two cut faces 218. Also shown on the strut 212 is a coating 220. As can be seen, the coating 220, covers only one face of the strut 212.

Figure 2B:
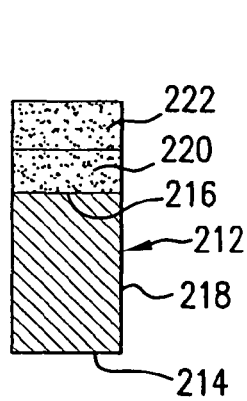
FIG. 2b is a cross-sectional view showing the coated strut of FIG. 2a after a second coating has been applied as may be employed in accord with the present invention.

FIG. 2b shows an example of how a coating 220 may also be applied in accord with the invention. In FIG. 2b, a first coating 220 and a second coating 222 have been applied to the strut 212. As can be seen, the first coating 220, is in contact with the strut 212 while the second coating 222 is in contact with the first coating 220 and further covers the outer surface 216 of the strut 212. This second coating 222 may be applied in accord with the processes and methods of the present invention. It may also be applied with different methods and processes. In this example, as well as with the others described herein, if a second coating 222 is employed this coating 222 may comprise the same materials as the first coating 220 and it may differ from the materials used for the first coating 220. In still other examples, which are not shown, the coating may be applied in other patterns as well. For example, it may be applied to opposing cut faces 218 and not the outer surface 216, likewise it may be applied to both cut faces 218 and the outer surface 216. In an exemplary embodiment, the outer surface 218 is coated and the two cut faces 218 as well as the inner surface 216 are not.

Figure 2C:
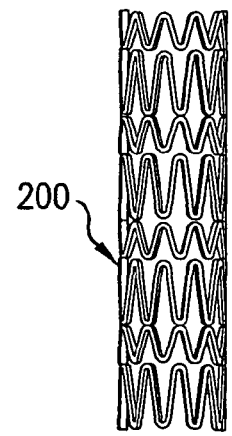
FIG. 2c is a side-view of an arterial stent coated in accord with the present invention.

FIG. 2c is a side view of an implantable aortic stent 200 that may be coated in accord with the present invention. The struts 212 shown in FIGS. 2a-2b are struts 212 that may comprise and make up this stent 200. The stent 200 may be self-expanding, mechanically expandable, or a hybrid stent which may have both self-expanding and mechanically expandable characteristics. The stent 200 may be made in a wide variety of designs and configurations, and may be made from a variety of materials including plastics and metals.

Various methods may be employed for delivery and implantation of the stent 200. For instance, a self-expanding stent may be positioned at the distal end of a catheter around a core lumen. Self-expanding stents may be typically held in an unexpanded state during delivery using a variety of methods including sheaths or sleeves which cover all or a portion of the stent. When the stent is in its desired location of the targeted vessel the sheath or sleeve is retracted to expose the stent which then self-expands upon retraction.

Another method includes mounting a mechanically expandable stent on an expandable member, such as a dilatation balloon provided on the distal end of an intravascular catheter, advancing the catheter through a patient's vasculature to the desired location within the patient's body lumen, and inflating the balloon on the catheter to expand the stent into a permanent expanded condition.

One method of inflating the balloon includes the use of inflation fluid. The expandable member is then deflated and the catheter removed from the body lumen, leaving the stent in the vessel to hold the vessel open.

While the workpiece shown in these initial figures is a stent, many other workpieces may be coated in accord with the invention. For example, other medical devices that may be coated include filters (e.g., vena cava filters), stent grafts, vascular grafts, intraluminal paving systems, implants and other devices used in connection with drug-loaded polymer coatings. Likewise, the workpeice may not be an implantable medical device but may, instead, be another piece that needs to be coated only on certain pre-selected surfaces. In some instances these medical devices or other workpieces may be made from conductive materials and in other instances they may not be. For example, they may be made from polymers or ceramics.

Figure 3:
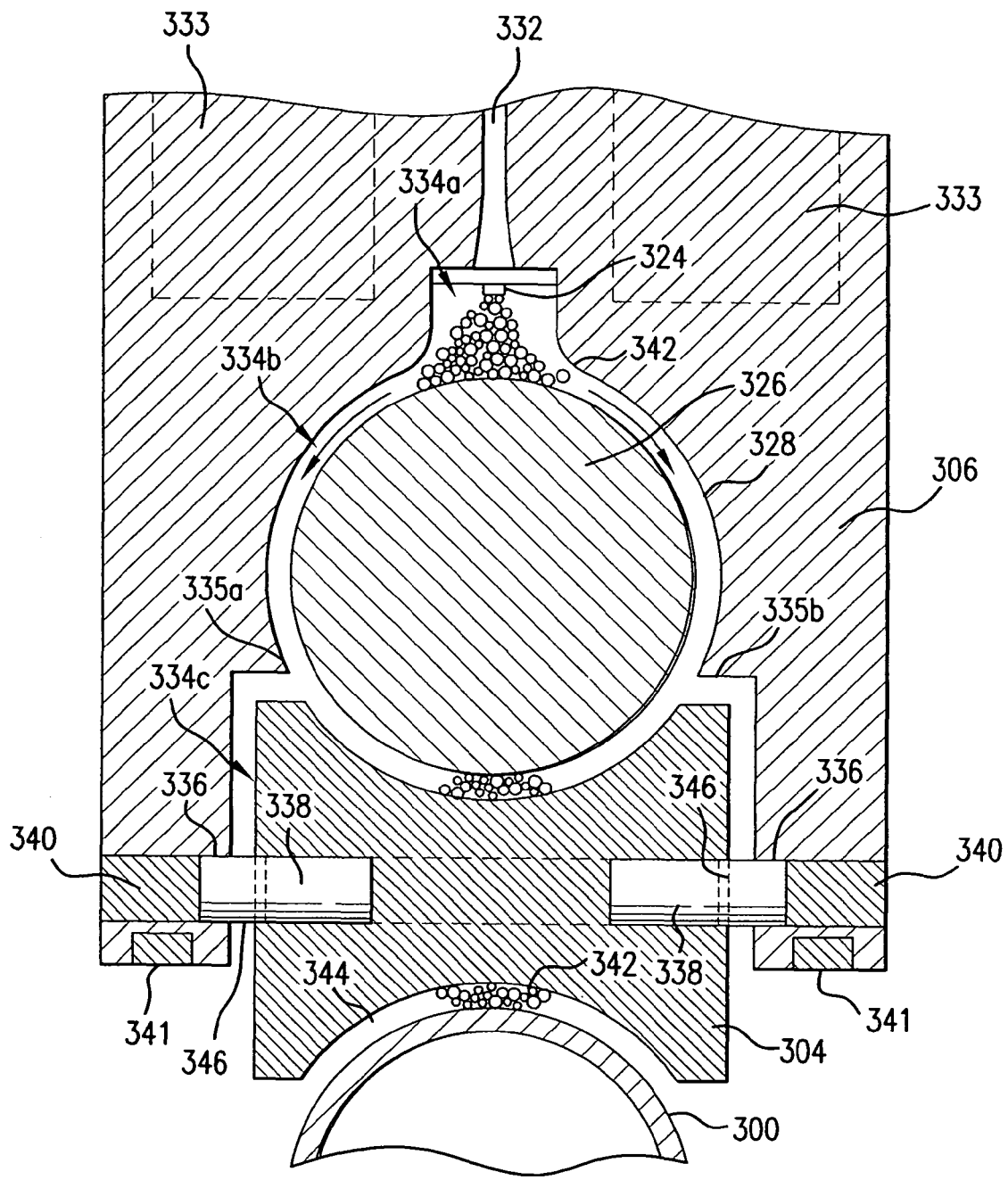
FIG. 3 is a enlarged side-view of a roller as may be employed in accord with the present invention.

FIG. 3 is an enlarged cross section of a distal end of an arm 306 as may be employed with the present invention. Visible in FIG. 3 are a dispensing member 324, a ball 326, a socket 328, a roller 304, a workpiece 300, a fluid passage 332, and an internal reservoir 333. The fluid passage 332 in this example is located in the arm 306 and is arranged vertically so that gravity can facilitate delivery of fluid resident in the passage 332. The end of the fluid passage 332, which is not shown, may be connected to an internal or external fluid source. In this instance, an internal reservoir 333 may be located in the arm 306. The reservoir 333 may include one or more recesses configured to store fluid. The reservoir 333 extends along opposite sides of the fluid passage 332 and fluidly communicates with the fluid passage 332. The arm 306 can be substantially hollow to store fluid and to reduce the weight of the arm 306. Although, in this instance, the fluid reservoir 333 recesses are positioned on either side of fluid passage 332, other arrangements are plausible. For example, one end of the fluid passage 332 may be connected to an external fluid source. For example, FIGS. 1a-1b illustrate a fluid passage 108 which may be connected to an external fluid source. As can also be seen in FIG. 3, the arm 306 may have a cut-out portion at one end. Here, the cut-out portion (334a-c) has a first section 334a, a second section 334b, and a third section 334c which may communicate with one another and form a passageway. The first section may form a rectangle while the second section may form a socket and the third section may for a concave recess. A dispensing member 324 may be located within the first section 334a while a ball 326 may be in the second section and a roller 304 may be in the third section 334c.

As noted, the second section 334b forms a socket that may receive a ball 326. The second section 334b may be substantially circular or any other suitable shape and the dimensions of the second section 334b may be slightly greater than the size of the ball 326. The second section 334b may also form two edges 335a-b. The distance between these two edges 335a-b may be slightly less than a diameter of the ball 326. As a result, the edges 335a-b, in combination with the dimensions of the second section 334b, maintain the ball 326 rotatably within the second section 334b while still allowing fluid from the passage 332 to pass around the ball 326.

As also seen in FIG. 3, the third section 334c, which may be generally C-shaped, may receive a portion of both the ball 326 and the roller 304. In other words, one side may be partially open to receive a portion of the ball 326 while the opposite open side may receive a portion of the roller 304. The two other sides may include recesses 336 to hold a shaft 338. In the example, the recesses 336 are cylindrical, however, other shapes and combinations of shapes may be used. As noted, each recess 336 may be sized to receive a portion of a roller shaft 338. In this example, the roller shaft 338 is cylindrical and extends through the entire roller 304. In other examples, individual roller shafts 338 may be positioned on opposite sides of the roller 304. The roller shaft 338 may be rotatable within the recess 336 and it may be slidable within the recess 336 as well. Each recess 336 may be sized to receive a biasing member 340 such as a spring. The roller shaft 338 may be biased inwardly by the biasing member 340 during operation.

As described herein, the dispensing member 324 may be located in the first section 334a. As seen in FIG. 3, coating 342 may be injected through an end of the fluid passage 332 through the dispensing member 324. Other alternative arrangements are also plausible. For example, the dispensing member 324 can be used to coat the outer surface of the ball 326 by various methods including, but not limited to needle injection, spraying, rolling, brushing, or spraying including atomized spray coating, and spray coating using an ultrasonic nozzle. In the instant case, once the coating 342 passes through the dispensing member 324, the coating 342 may be applied to an outer surface of the ball 326. In the example, the dispensing member 324 is orientated vertically and may use hydraulic pressure to facilitate delivery.

The ball 326 may be any of a variety of shapes and sizes. In the instant case, the ball 326 is circular while in other embodiments it may contain dimples or channels of some kind. The size of the ball 326 and the socket 328 opening can be changed to vary the coating thickness. For example, the farther the ball 326 protrudes from the socket 328, the more surface area the roller 304 of the ball 326 may cover.

The dispensing member 324 dispenses coating to the ball 326. In the instant case, the ball 326 may be interposed between the dispensing member 324 and the roller 304 to facilitate uniform coating 342 thickness. The ball 326 may rotate freely and, thus, roll out the coating 342 as the coating 342 is delivered from the reservoir 333 via the fluid passage 332. The coating 342 may be delivered intermittently or continuously during this process. The ball 326 may be maintained between the dispensing member 324 and the roller 304 by the socket 328. The socket 328 allows limited rotational movement of the ball 306. The edges 335a of the socket 328 may prevent more than only a portion of the ball 326 from moving outside of the socket 328. The socket 328 allows the ball 326 to rotate while simultaneously acting as a seal to limit air from reaching the coating stored in the reservoir 333 and the fluid passage 332. As the roller 304 contacts the workpiece, the ball 326 may rotate. Meanwhile, the dispensing member 324 may deliver coating 342 to an outer surface of the ball 326.

FIG. 3 also shows a roller 304 in accord with the invention. The roller 304 may include a continuous concave shaped outer surface 344. The outer surface 344 of the roller 304 can be any shape, however, preferably the roller 304 may be shaped to matingly contact the outer surface of the ball 326. As the roller 304 rotates, the outer surface 344 contacts the ball 326 and coating 342 may be transferred. Meanwhile, the coated roller 304 in turn coats the workpiece 300. The arm 306 and/or the workpiece 300 can be moved to impart rotation to the ball 326 and the roller 304. In the instant case, the arm 306 may be moved longitudinally, however, other directions are plausible. Accordingly, a target surface of the workpiece 300 may be coated. This may be accomplished by timing the dispensing of coating from the roller and the movement of the roller across the workpiece. In this example, half the outer surface of the workpiece 300 may be coated.

Also as seen in FIG. 3, bearings 346, such as smooth metal balls or rollers, may be provided to reduce friction. Any suitable bearing 346 can be used including ball bearings, roller bearings, thrust bearings, and combinations of the same.

Figure 4:
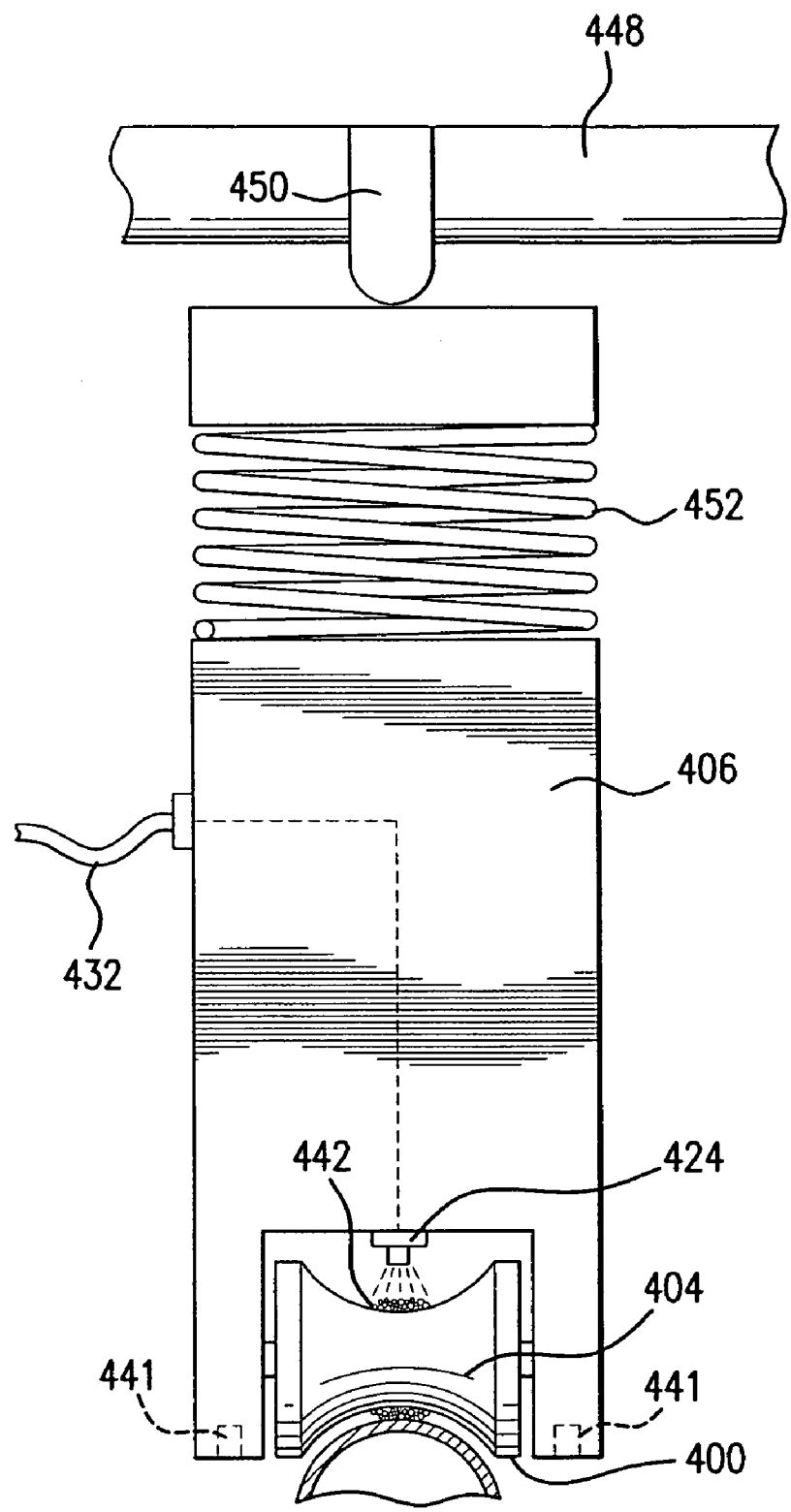
FIG. 4 is a side-view of a follower mechanism and a roller as may be employed in accord with the present invention.

The arm 306 may also be provided with sensors 341. The sensors 341 may communicate with a follower mechanism (FIG. 4). Any suitable sensor 341 may be used including pressure, capacitance, and infrared sensors. The sensors 341 may be pre-set to sense irregularities. For example, deviations from a predetermined range of distances from the roller 304 to the workpiece 300 may be detected. The sensor 341 detects changes in pressure, capacitance, or by using a beam of infrared light to compute the distance to the workpiece 300 from characteristics of the returned signal. The sensor 341 may then send a signal to a follower mechanism to adjust the position of the arm 306.

FIG. 4 is a side-view of a follower mechanism 448, an arm 406, a dispensing member 424, a roller 404, a fluid passage 432, and a workpiece 400 as may be employed in accord with the invention.

In the example, the dispensing member 424 is configured for a spray coating application. Spraying parameters such as atomization pressure and the distance between the dispensing member 424 nozzle and the roller 404 can be adjusted to vary the thickness of the coating 442. Although spray coating is shown, as described herein, various dispensing members can be used to coat the outer surface of the roller 404.

The dispensing member 424 may be located at one end of the fluid passage 432. In this example, the fluid passage 432 can be connected to an external fluid source. Fluid can be provided to the dispensing member 424 via the fluid passage 432 by any suitable means including, but not limited to, gravity and or hydraulic pressure. In this example, the dispensing member 424 may directly coat an outer surface of the roller 404. Meanwhile, the outer surface of the roller 404 may contact and coat a target surface of the workpiece 400.

In this example, a portion of the arm 406 may be biased via a biasing member 452. The biasing member 452 can be any suitable member such as a spring. The biasing member 452 is configured to expand and contract to facilitate an even distribution of coating 442 on the workpiece 400.

As seen in FIG. 4, a follower mechanism 448 may also be provided. The follower mechanism 448 may receive commands from the sensor 441, types of which are described herein in detail. Accordingly, upon receiving a command from the sensor 441, the follower mechanism 448 may adjustment a position of the arm 406 via a lobe 450. In the instant case, when the follower mechanism 448 rotates, the lobe 450 may also rotate. The lobe 450 may be shaped so that when it rotates, the arm 406 is forced inwardly or outwardly. Consequently, the roller 404 may be adjusted by moving toward or away from the workpiece 400. Other types of follower mechanisms 448 may also be used.

The follower mechanism 448 may be provided to adjust the position of the arm 306. More specifically, the follower mechanism 448 may change rotary motion into linear motion of the arm 406 to compensate for surface irregularities of the workpiece. The follower mechanism 448 may be provided with the spring 452, or each component can be provided individually. Moreover, the device may include an arrangement where a follower mechanism 448 and/or a spring 452 are not provided.

Figure 5:
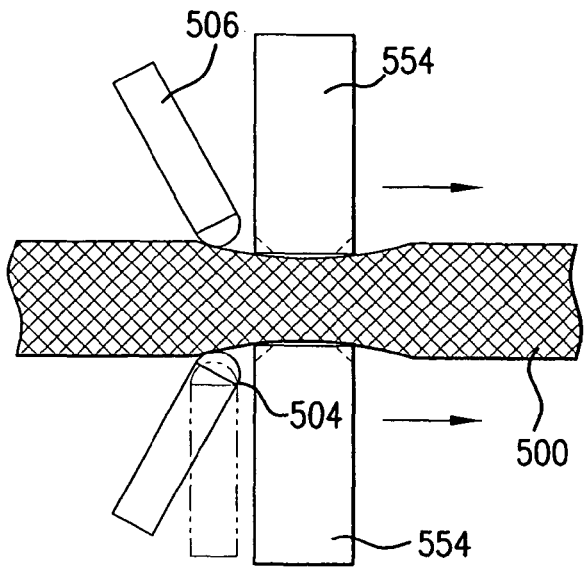
FIG. 5 is a side-view of a plurality of rollers, a workpiece, and a reducing orifice as may be employed in accord with the present invention.

FIG. 5 shows a plurality of arms 506, a plurality of rollers 504, a workpiece 500, and a reducing orifice 554 which may be employed in accord with the embodiments of the present invention. The reducing orifice 554 may also be used to assist in maintaining a constant distance between the rollers 504 and the workpiece 500.

In this example, the reducing orifice 554 precedes the rollers 504 as the rollers 504 move along the workpiece 500 in a longitudinal direction, but any arrangement may be used. For example, the workpiece 500 may be moved through a stationary reducing orifice 554. As the reducing orifice 554 moves over the workpiece 500, the diameter of the workpiece 500 may be reduced slightly. As each portion of the workpiece 500 exits the reducing orifice 554, the rollers 504 coat a target surface of the workpiece 500 at a predetermined distance. Since the target surface of the workpiece 500 may be held in about the same radial position relative to the reducing orifice 554, the reducing orifice 554 may eliminate irregularities that may arise when coating the target surface of the workpiece 500. For instance, bare spots and variations forming on the target surface may be reduced.

In FIG. 5, the rollers are positioned at an angle to the longitudinal axis of the workpiece 500, however, any arrangement is plausible. For example, the dashed lines in FIG. 5 show a roller 504 arranged perpendicularly with respect to the longitudinal axis of the workpiece 500. Also as seen in FIG. 5, the edges of the reducing orifice 554 may be chamfered to facilitate the entry and exit of the workpiece 500. The chamfered sections are indicated by dashed lines.

Figure 6A:
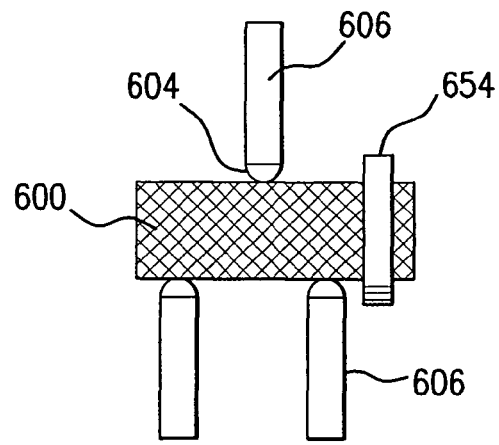
FIG. 6a is a top view of a plurality of offset rollers, a workpiece, and a reducing orifice that may be employed in accord with the present invention.

As seen in FIG. 6a, the plurality of rollers 604 may also be offset from one another. Off-setting or overlapping the rollers 604 may facilitate in coverage of surface area in order to avoid an edge effect. In this instant case, the rollers 604 are staggered longitudinally.

Figure 6B:
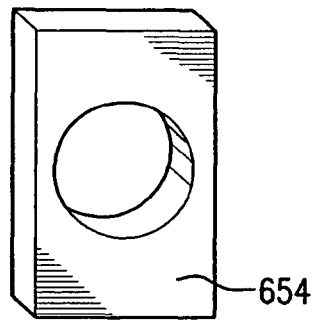
FIG. 6b is a front-view of a plate having a reducing orifice as may be employed to coat a workpiece in accord with the present invention.
Figure 6C:
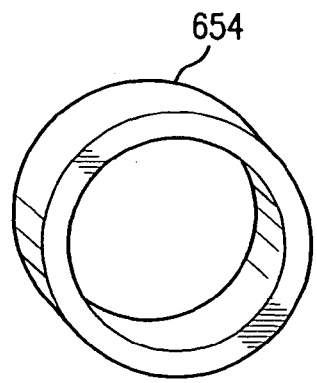
FIG. 6c is another front-view of a tube having a reducing orifice as may be employed to coat a workpiece in accord with the present invention.

As seen in FIGS. 6b and 6c, the reducing orifice 604 can be any suitable size or shape. For example, the reducing orifice 654 may be a plate with a circular hole or a tube with a predetermined diameter in accord with the embodiments. Additionally, the reducing orifice may comprise a set of concave rollers (not shown).

Figure 7:
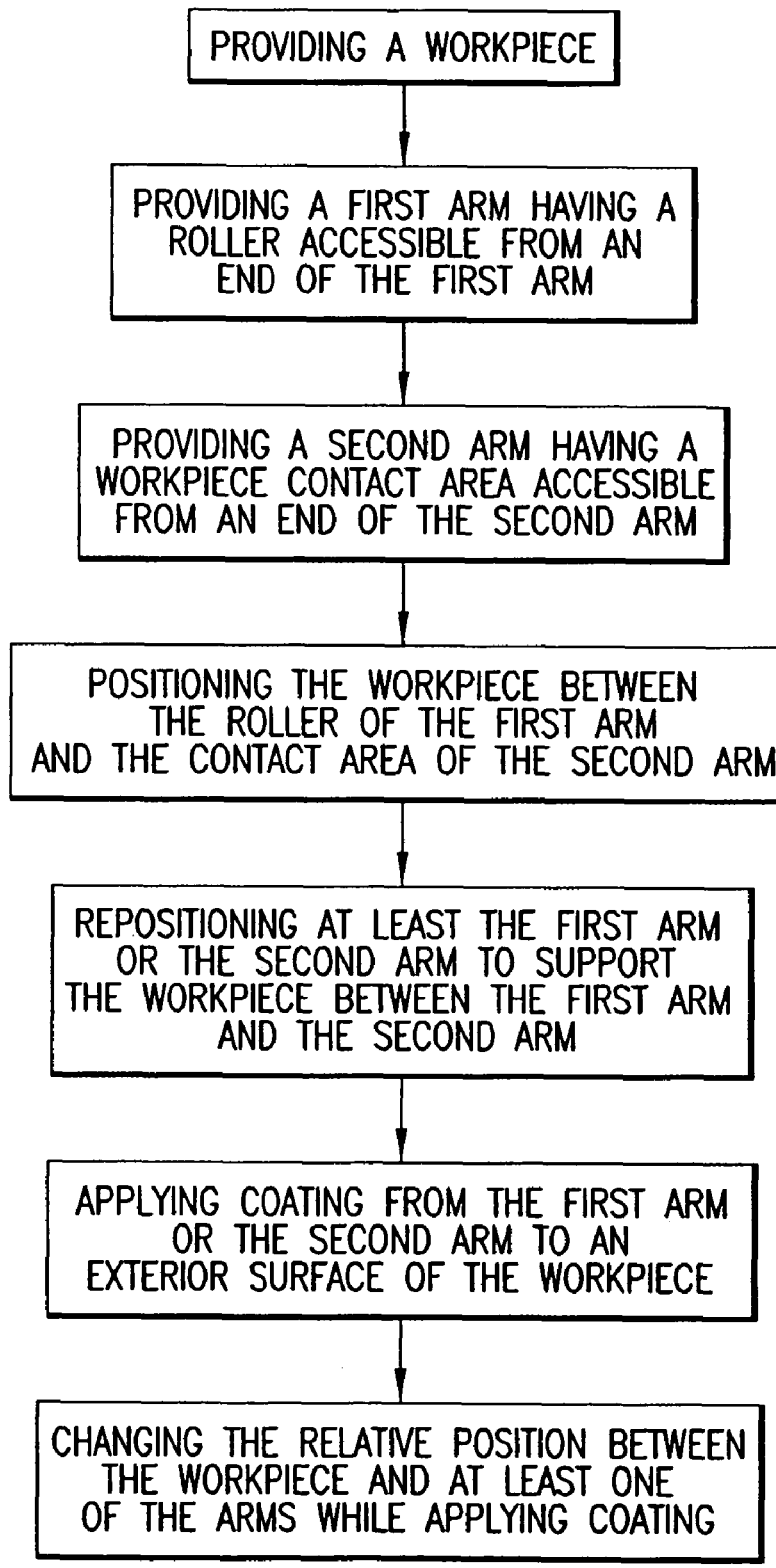
FIG. 7 shows a flowchart of a method for coating a workpiece that may be employed with the present invention.

FIG. 7 shows a flowchart illustrating a method of coating a workpiece that may be employed with the present invention. Step 1 of the method is to provide a workpiece. Steps 2 and 3 of the method generally involve providing a first arm having a roller accessible from an end of the first arm and providing a second arm having a workpiece contact area accessible from an end of the second arm. Then, in Step 4, the workpiece may be positioned between the roller of the first arm and the contact area of the second arm. If desired, as illustrated in Step 5, the first arm or the second arm may be repositioned throughout the method to support the workpiece between the first arm and the second arm. As shown in Step 6, a coating may be applied from the first arm or the second arm to an exterior surface of the workpiece. Further, as shown in Step 7, the relative position between the workpiece and at least one of the arms may be changed throughout the method, as desired, while applying the coating. The method described and disclosed may also be performed in various sequences, with some or all of the disclosed steps being performed in a different order than described while still remaining within the spirit and scope of the present invention.

It should be understood that the foregoing descriptions of various examples of the roller, arm, reducing orifice, and dispensing member are not intended to be limiting, and any number of modifications, combinations, and alternatives of the examples may be employed to facilitate the effectiveness of the coating of target surfaces of the workpiece.

The coating, in accord with the embodiments of the present invention, may comprise a polymeric and or therapeutic agent formed, for example, by admixing a drug agent with a liquid polymer, in the absence of a solvent, to form a liquid polymer/ drug agent mixture. A suitable list of drugs and/or polymer combinations is listed below. The term "therapeutic agent" as used herein includes one or more "therapeutic agents" or "drugs". The terms "therapeutic agents" or "drugs" can be used interchangeably herein and include pharmaceutically active compounds, nucleic acids with and without carrier vectors such as lipids, compacting agents (such as histones), viruses (such as adenovirus, andenoassociated virus, retrovirus, lentivirus and α-virus), polymers, hyaluronic acid, proteins, cells and the like, with or without targeting sequences.

Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; anti-proliferative agents such as enoxaprin, angiopeptin, rapamycin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/anti-proliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaprin, hirudin, Warfarin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vasoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the insertion site. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor $\forall$ and $\exists$, platelet-derived endothelial growth factor, platelet-derived growth factor, tumor necrosis factor $\forall$, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

As stated above, coatings used with the exemplary embodiments of the present invention may comprise a polymeric material/drug agent matrix formed, for example, by admixing a drug agent with a liquid polymer, in the absence of a solvent, to form a liquid polymer/drug agent mixture. Curing of the mixture typically occurs in-situ. To facilitate curing, a cross-linking or curing agent may be added to the mixture prior to application thereof. Addition of the cross-linking or curing agent to the polymer/drug agent liquid mixture must not occur too far in advance of the application of the mixture in order to avoid over-curing of the mixture prior to application thereof. Curing may also occur in-situ by exposing the polymer/drug agent mixture, after application to the luminal surface, to radiation such as ultraviolet radiation or laser light, heat, or by contact with metabolic fluids such as water at the site where the mixture has been applied to the luminal surface. In coating systems employed in conjunction with the present invention, the polymeric material may be either bioabsorbable or biostable. Any of the polymers described herein that may be formulated as a liquid may be used to form the polymer/drug agent mixture.

In accord with the embodiments, the polymer used to coat the medical device is provided in the form of a coating on an expandable portion of a medical device. After applying the drug solution to the polymer and evaporating the volatile solvent from the polymer, the medical device is inserted into a body lumen where it is positioned to a target location. In the case of a balloon catheter, the expandable portion of the catheter is subsequently expanded to bring the drug-impregnated polymer coating into contact with the lumen wall. The drug is released from the polymer as it slowly dissolves into the aqueous bodily fluids and diffuses out of the polymer. This enables administration of the drug to be site-specific, limiting the exposure of the rest of the body to the drug.

The polymer used in the exemplary embodiments of the present invention is preferably capable of absorbing a substantial amount of drug solution. When applied as a coating on a medical device in accordance with the present invention, the dry polymer is typically on the order of from about 1 to about 50 microns thick. In the case of a balloon catheter, the thickness is preferably about 1 to 10 microns thick, and more preferably about 2 to 5 microns. Very thin polymer coatings, e.g., of about 0.2-0.3 microns and much thicker coatings, e.g., more than 10 microns, are also possible. It is also within the scope of the present invention to apply multiple layers of polymer coating onto a medical device. Such multiple layers are of the same or different polymer materials.

The polymer of the present invention may be hydrophilic or hydrophobic, and may be selected from the group consisting of polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Coatings from polymer dispersions such as polyurethane dispersions (BAYHDROL®, etc.) and acrylic latex dispersions are also within the scope of the present invention. The polymer may be a protein polymer, fibrin, collagen and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In one embodiment of the invention, the preferred polymer is polyacrylic acid, available as HYDROPLUS® (Boston Scientific Corporation, Natick, Mass.), and described in U.S. Pat. No. 5,091,205, the disclosure of which is hereby incorporated herein by reference. U.S. Pat. No. 5,091,205 describes medical devices coated with one or more polyisocyanates such that the devices become instantly lubricious when exposed to body fluids. In another preferred embodiment of the invention, the polymer is a copolymer of polylactic acid and polycaprolactone.

The examples described herein are merely illustrative, as numerous other embodiments may be implemented without departing from the spirit and scope of the exemplary embodiments of the present invention. Moreover, while certain features of the invention may be shown on only certain embodiments or configurations, these features may be exchanged, added, and removed from and between the various embodiments or configurations while remaining within the scope of the invention. Likewise, methods described and disclosed may also be performed in various sequences, with some or all of the disclosed steps being performed in a different order than described while still remaining within the spirit and scope of the present invention.

What is claimed is:

1. A method of coating a workpiece, the method comprising:
   providing a workpiece;
   providing a first arm having a roller accessible from an end of the first arm, wherein the first arm contains a fluid passage and the roller is in fluid communication with a ball positioned within a socket;
   providing a second arm having a workpiece contact area accessible from an end of the second arm;
   positioning the workpiece between the roller of the first arm and the contact area of the second arm;
   repositioning at least the first arm or the second arm to support the workpiece between the first arm and the second arm;
   applying a coating from the first arm or the second arm to an exterior surface of the workpiece; and
   changing a relative position between the workpiece and at least one of the arms while applying the coating.

2. The method of claim 1 further comprising:
   squeezing the workpiece to reduce a cross-sectional profile of the workpiece prior to applying coating to an exterior surface of the workpiece.

3. The method of claim 2 wherein squeezing the workpiece to reduce a cross-sectional profile of the workpiece prior to applying coating to an exterior surface of the workpiece includes moving the workpiece through an aperture.

4. The method of claim 1 wherein the first arm and the second arm are slidable from a first open position to a second closed position.

5. The method of claim 1 wherein changing the relative position between the workpiece and at least one of the arms while applying coating includes movement of the roller of the first arm along an exterior surface of the workpiece.

6. The method of claim 1 wherein the first arm is moveable on a first plane of reference and the second arm is moveable on a second plane of reference and the first plane of reference and the second plane of reference are parallel to one another.

7. The method of claim 1 wherein the contact area of the second arm contains a roller for contacting the workpiece.

8. The method of claim 1 wherein the coating is applied intermittently to an exterior surface of the workpiece.

9. The method of claim 1 wherein the contact area of the second arm includes a roller accessible from an end of the second arm.

10. The method of claim 9 wherein the roller of the first arm and the roller of the second arm are sized to contact only a portion of an external surface of the workpiece.

11. The method of claim 1 wherein the first arm is moveable on a plane of reference and the second arm is moveable on the same plane of reference.

12. The method of claim 1 wherein the first arm and the second arm are axially aligned with each other.

13. The method of claim 1 wherein the first arm and the second arm are axially offset from one another.

14. The method of claim 1 wherein the coating is delivered through the fluid passage under pressures greater than atmospheric pressure.

15. The method of claim 1 further comprising:
   using a follower mechanism and signals from a sensor to reposition the first arm.

16. The method of claim 1 wherein the workpiece contains a lattice portion.

17. The method of claim 1 wherein the workpiece is a medical device.

18. The method of claim 17 wherein the medical device is a stent.

19. The method of claim 17 wherein the coating contains a therapeutic.

* * * * *